(12) United States Patent
Velvadapu et al.

(10) Patent No.: US 12,000,784 B2
(45) Date of Patent: Jun. 4, 2024

(54) IDENTIFICATION OF DEGRADATIVE SPECIES

(71) Applicant: Senseonics, Incorporated, Germantown, MD (US)

(72) Inventors: Venkata Velvadapu, Germantown, MD (US); Mark Mortellaro, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 512 days.

(21) Appl. No.: 17/097,678

(22) Filed: Nov. 13, 2020

(65) Prior Publication Data

US 2021/0140888 A1     May 13, 2021

Related U.S. Application Data

(60) Provisional application No. 62/934,599, filed on Nov. 13, 2019.

(51) Int. Cl.

| | | |
|---|---|---|
| *G01N 21/64* | (2006.01) | |
| *A61B 5/145* | (2006.01) | |
| *A61B 5/1486* | (2006.01) | |
| *G01N 21/78* | (2006.01) | |
| *G01N 33/52* | (2006.01) | |
| *G01N 33/66* | (2006.01) | |

(52) U.S. Cl.
CPC ..... *G01N 21/6428* (2013.01); *A61B 5/14532* (2013.01); *A61B 5/14865* (2013.01); *G01N 33/521* (2013.01); *G01N 33/66* (2013.01); *A61B 2503/40* (2013.01); *G01N 2021/6439* (2013.01)

(58) Field of Classification Search
CPC .. G01N 21/6428; G01N 33/521; G01N 33/66; G01N 2021/6439; G01N 2021/7786; G01N 21/78; A61B 5/14532; A61B 5/14865; A61B 2503/40; A61B 5/0075; A61B 5/14735; A61B 5/686
See application file for complete search history.

(56) References Cited

U.S. PATENT DOCUMENTS

| | | | |
|---|---|---|---|
| 9,414,775 B2 * | 8/2016 | Colvin, Jr. ......... | A61B 5/14556 |
| 9,693,714 B2 | 7/2017 | DeHennis et al. | |
| 9,931,068 B2 | 4/2018 | Huffstetler et al. | |
| 10,827,962 B2 * | 11/2020 | Dehennis ............. | A61B 5/1495 |
| 2013/0241745 A1 | 9/2013 | Calvin, Jr. et al. | |
| 2018/0303387 A1 * | 10/2018 | Dehennis ........... | A61B 5/14556 |
| 2023/0103609 A1 * | 4/2023 | Dehennis ........... | A61B 5/14556 |
| | | | 600/317 |

FOREIGN PATENT DOCUMENTS

| | | |
|---|---|---|
| CN | 107353300 A | 11/2017 |
| WO | 2015/128622 A1 | 9/2015 |

OTHER PUBLICATIONS

Debski et al. "Mechanism of oxidative conversion of Amplexs Red to resorufin: Pulse radiolysis and enzymatic studies", Free Radical Biology and Medicine, vol. 95, pp. 323-332, published Mar. 26, 2016. (Year: 2016).*
Wardman, Peter, "Fluorescent and luminescent probes for measurement of oxidative and nitrosative species in cells and tissues: progress, pitfalls, and prospects", Free Radical Biology & Medicine, vol. 43, No. 7, (2007) 995-1022.
SchÄferling, Michael, et al., "Luminescent probes for detection and imaging of hydrogen peroxide", Microchim Acta, (2011) 174:1-18.
Zielonka, Jacek, et al., "Small-molecule luminescent probes for the detection of cellular oxidizing and nitrating species", Free Radical Biology & Medicine, vol. 128, (2018) 3-22.
Winterbourn, Christine C, "The challenges of using fluorescent probes to detect and quantify specific reactive oxygen species in living cells", Biochimica et Biophysica Acta, vol. 1840, No. 2 (2014) 730-738.
Yudhistira, Tesla, et al., "Imaging of Hypochlorous Acid by Fluorescence and Applications in Biological Systems", Chemistry an Asian Journal Review, vol. 14, No. 18 (2019) 3048-3084.

* cited by examiner

*Primary Examiner* — Shafiqul Haq
*Assistant Examiner* — Nam P Nguyen
(74) *Attorney, Agent, or Firm* — Rothwell, Figg, Ernst & Manbeck, P.C.

(57) ABSTRACT

A sensor (e.g., an optical sensor) that may be implanted within a living animal (e.g., a human) and may be used to measure an analyte (e.g., glucose or oxygen) in a medium (e.g., interstitial fluid, blood, or intraperitoneal fluid) within the animal. The sensor may include a sensor substrate, electrode or housing, an analyte indicator covering at least a portion of the sensor, and one or more probes that identify degradative species in an environment of the sensor.

34 Claims, 8 Drawing Sheets

IDENTIFICATION OF DEGRADATIVE SPECIES

CROSS-REFERENCE TO RELATED APPLICATION

The present application claims the benefit of priority to U.S. Provisional Application Ser. No. 62/934,599, filed on Nov. 13, 2019, which is incorporated herein by reference in its entirety.

BACKGROUND

Field of Invention

The present invention relates generally to detecting, identifying, trapping, isolating, sequestering, neutralizing, inactivating, and/or inhibiting degradative species that interact with analyte sensor moieties when measuring an analyte in a medium of a living animal using a system including a sensor implanted (partially or fully) or inserted into the living animal. Specifically, the present invention relates to a sensor that utilizes one or more probes, which may be incorporated within an analyte indicator, and/or a material covering at least a portion of the analyte indicator, in order to detect, identify, trap, isolate, sequester, neutralize, inactivate, and/or inhibit degradative species that interact with analyte sensor moieties.

Discussion of the Background

A sensor may be implanted (partially or fully) within a living animal (e.g., a human) and used to measure an analyte (e.g., glucose, oxygen, cardiac markers, low-density lipoprotein (LDL), high-density lipoprotein (HDL), or triglycerides) in a medium (e.g., interstitial fluid (ISF), blood, or intraperitoneal fluid) within the living animal. The sensor may include a light source (e.g., a light-emitting diode (LED) or other light emitting element), indicator molecules, and a photodetector (e.g., a photodiode, phototransistor, photoresistor or other photosensitive element). Examples of implantable sensors employing indicator molecules to measure an analyte are described in U.S. Pat. Nos. 5,517,313 and 5,512,246, which are incorporated herein by reference in their entirety.

A sensor may include an analyte indicator, which may be in the form of indicator molecules embedded in a graft (i.e., layer or matrix). For example, in an implantable fluorescence-based glucose sensor, fluorescent indicator molecules may reversibly bind glucose and, when irradiated with excitation light (e.g., light having a wavelength of approximately 378 nm), emit an amount of light (e.g., light in the range of 400 to 500 nm) that depends on whether glucose is bound to the indicator molecule.

If a sensor is implanted in the body of a living animal, the animal's immune system may begin to attack the sensor. For instance, if a sensor is implanted in a human, white blood cells may attack the sensor as a foreign body, and, in the initial immune system onslaught, neutrophils may be the primary white blood cells attacking the sensor. The defense mechanism of neutrophils includes the release of highly caustic substances known as reactive oxygen species. For instance, in indicator molecules having a boronate group, degradative species may degrade the indicator molecules by oxidizing the boronate group, thus disabling the ability of the indicator molecule to bind glucose.

Known reactive oxygen species include, for example, hydrogen peroxide and superoxide. While it has been postulated that hydrogen peroxide and other reactive species such as reactive oxygen species (ROS) and reactive nitrogen species (RNS) may degrade the indicator molecules of an analyte indicator, there is no experimental evidence that has identified the degradative species that react with the indicator. Further, prior to the invention of the present disclosure, there has been no device or method for detecting and identifying the degradative species that react with indicator molecules in an implantable medical device or sensor. Most of the ROS/RNS that get generated are short lived and, depending on factors such as location, proximity, diffusion and the nature of environment, may or may not influence the degradation profiles.

There is presently a need in the art for a method for detecting, identifying, trapping, isolating, sequestering, neutralizing, inactivating, and/or inhibiting degradative species that interact with analyte sensor moieties when measuring an analyte in a medium of a living animal using a system including a sensor implanted (partially or fully) or inserted into the living animal. Also, there is a need in the art for continuous analyte sensors having increased longevity.

SUMMARY

The present invention provides a method for detecting, identifying, trapping, isolating, sequestering, neutralizing, inactivating, and/or inhibiting degradative species that interact with analyte sensor moieties when measuring an analyte in a medium of a living animal using a system including a sensor implanted (partially or fully) or inserted into the living animal.

One aspect of the present invention provides a sensor that may be for implantation or insertion within a living animal and measurement of an analyte in a medium within the living animal. The sensor may include an analyte indicator and one or more selective degradative species probes that can be utilized to understand their reactivity against the corresponding degradative species generated around the device. In some embodiments, the sensor may include multiple selective degradative species probes, each of which has distinct characteristic absorption and emission properties so as to detect different degradative species. In some embodiments, the analyte indicator and one or more degradative species probes are provided on a substrate. The substrate may be an electrode or a sensor surface. In some embodiments, the sensor may include a sensor housing, and the analyte indicator may cover at least a portion of the sensor housing.

In some embodiments, the sensor may include at least one probe-containing polymer graft, and the one or more degradative species probes may be co-polymerized with, entrapped in, or dispersed within the probe-containing polymer graft. In some embodiments, the probe-containing polymer graft may cover at least a portion of the sensor housing. In some embodiments, the probe-containing polymer graft may be within the sensor housing.

In some embodiments, the one or more degradative species probes may be incorporated with the analyte indicator, e.g., as a co-monomer. In some embodiments, the sensor may include a material, e.g., a membrane, covering at least a portion of the analyte indicator, and the one or more degradative species probes are incorporated within the material.

In some embodiments, the present disclosure provides a sensor for measurement of an analyte in a medium within a living animal, the sensor comprising: an analyte indicator; and one or more degradative species probes, wherein the degradative species probes have absorption and/or emission profiles that are selective for a specific degradative species.

In some embodiments, the present disclosure provides a method of fabricating a sensor for measurement of an analyte in a medium within a living animal, the method comprising: applying an analyte indicator to a sensor such that the applied analyte indicator covers at least a portion of the sensor, wherein the analyte indicator comprises one or more degradative species probes, wherein the degradative species probes have absorption and/or emission profiles that are selective for a specific degradative species.

In some embodiments, the present disclosure provides a method of detecting and identifying changes in degradative species in an in vivo environment of an implanted medical device comprising: a) implanting a sensor of the present disclosure into an animal; b) explanting the sensor at a defined time point; c) characterizing changes to absorption/emission properties of the one or more degradative species probes compared to absorption/emission properties of the one or more degradative species probes prior to implanting; and d) quantifying reactivity of the one or more degradative species probes with one or more degradative species.

In some embodiments, the present disclosure provides a method of screening compounds for inclusion in an implantable sensor comprising: applying an analyte indicator to a sensor such that the applied analyte indicator covers at least a portion of the sensor, wherein the analyte indicator comprises one or more degradative species probes, wherein the degradative species probes have absorption and/or emission profiles that are selective for a specific degradative species; applying a test compound to the sensor to form a test sensor; implanting the test sensor into an animal; explanting the sensor at a defined time point; characterizing changes to absorption/emission properties of the one or more degradative species probes compared to absorption/emission properties of the one or more degradative species probes prior to implanting; and comparing the characterized changes to the absorption/emission properties of the one or more degradative species probes to characterized absorption/emission properties of the one or more degradative species probes in a control sensor, wherein the control sensor did not include the test compound; and detecting whether presence the test compound increased or decreased degradative species in an in vivo environment of the implantable sensor.

In some embodiments, the present disclosure provides a method of screening compounds for inclusion in an implantable sensor comprising: applying an analyte indicator to a sensor such that the applied analyte indicator covers at least a portion of the sensor, wherein the analyte indicator comprises one or more degradative species probes, wherein the degradative species probes have absorption and/or emission profiles that are selective for a specific degradative species; applying a test compound to the sensor to form a test sensor; performing an in vitro test simulating physiological conditions for a defined time period; characterizing changes to absorption/emission properties of the one or more degradative species probes compared to absorption/emission properties of the one or more degradative species probes prior to performing the in vitro test; and comparing the characterized changes to the absorption/emission properties of the one or more degradative species probes to characterized absorption/emission properties of the one or more degradative species probes in a control sensor, wherein the control sensor did not include the test compound; and detecting whether presence the test compound increased or decreased degradative species.

In some embodiments, the present disclosure provides a method of identifying and/or quantifying degradative species in an environment of a medical device comprising: applying an analyte indicator to a sensor such that the applied analyte indicator covers at least a portion of the sensor, wherein the analyte indicator comprises one or more degradative species probes, wherein the degradative species probes have absorption and/or emission profiles that are selective for a specific degradative species; exposing the sensor to an environment containing degradative species; characterizing changes to absorption/emission properties of the one or more degradative species probes compared to absorption/emission properties of the one or more degradative species probes prior to the exposing step; and quantifying reactivity of the one or more degradative species probes with one or more degradative species.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
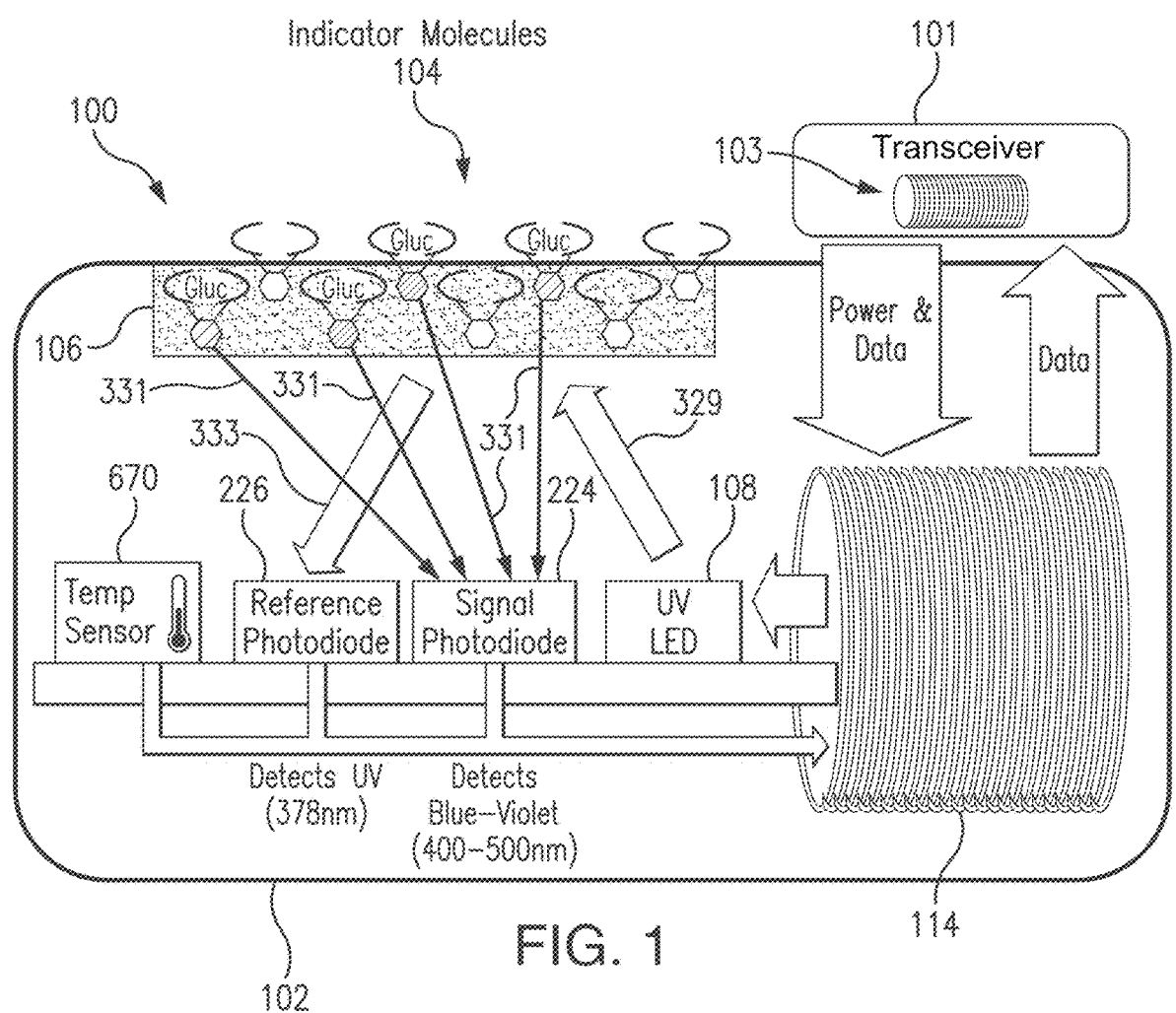
FIG. 1 is a schematic view illustrating a sensor system embodying aspects of the present invention.

FIG. 1 is a schematic view of a sensor system embodying aspects of the present invention. In some non-limiting embodiments, as shown in FIG. 1, the system may include a sensor 100 and an external transceiver 101. In some embodiments, the sensor 100 may be an implantable sensor configured to be fully or partially implanted in a living animal (e.g., a living human). The sensor 100 may be implanted, for example, in a living animal's arm, wrist, leg, abdomen, peritoneum, or other region of the living animal suitable for sensor implantation. For example, in some non-limiting embodiments, the sensor 100 may be implanted beneath the skin (i.e., in the subcutaneous or peritoneal tissues). However, this is not required, and, in some alternative embodiments, the sensor 100 may be a transcutaneous sensor.

In some embodiments, a transceiver 101 may be an electronic device that communicates with the sensor 100 to power the sensor 100, provide commands and/or data to the sensor 100, and/or receive data from the sensor 100. In some embodiments, the received data may include one or more sensor measurements. In some embodiments, the sensor measurements may include, for example and without limitation, one or more light measurements from one or more photodetectors of the sensor 100 and/or one or more temperature measurements from one or more temperature sensors of the sensor 100. In some embodiments, the transceiver 101 may calculate analyte (e.g., glucose) concentrations from the measurement information received from the sensor 100.

In some non-limiting embodiments, the transceiver 101 may be a handheld device or an on-body/wearable device. For example, in some embodiments where the transceiver 101 is an on-body/wearable device, the transceiver 101 may be held in place by a band (e.g., an armband or wristband) and/or adhesive, and the transceiver 101 may convey (e.g., periodically, such as every two minutes, and/or upon user initiation) measurement commands (i.e., requests for measurement information) to the sensor 100. In some embodiments where the transceiver 101 is a handheld device, positioning (i.e., hovering or swiping/waving/passing) the transceiver 101 within range over the sensor implant site (i.e., within proximity of the sensor 100) may cause the transceiver 101 to automatically convey a measurement command to the sensor 100 and receive a data from the sensor 100.

In some embodiments, as shown in FIG. 1, the transceiver 101 may include an inductive element 103, such as, for example, a coil. In some embodiments, the transceiver 101 may generate an electromagnetic wave or electrodynamic field (e.g., by using a coil) to induce a current in an inductive element 114 of the sensor 100. In some non-limiting embodiments, the sensor 100 may use the current induced in the inductive element 114 to power the sensor 100. However, this is not required, and, in some alternative embodiments, the sensor 100 may be powered by an internal power source (e.g., a battery).

In some embodiments, the transceiver 101 may convey data (e.g., commands) to the sensor 100. For example, in some non-limiting embodiments, the transceiver 101 may convey data by modulating the electromagnetic wave generated by the inductive element 103 (e.g., by modulating the current flowing through the inductive element 103 of the transceiver 101). In some embodiments, the sensor 100 may detect/extract the modulation in the electromagnetic wave generated by the transceiver 101. Moreover, the transceiver 101 may receive data (e.g., one or more sensor measurements) from the sensor 100. For example, in some non-limiting embodiments, the transceiver 101 may receive data by detecting modulations in the electromagnetic wave generated by the sensor 100, e.g., by detecting modulations in the current flowing through the inductive element 103 of the transceiver 101.

In some embodiments, as shown in FIG. 1, the sensor 100 may include a sensor housing 102 (i.e., body, shell, capsule, or encasement), which may be rigid and biocompatible. In exemplary embodiments, sensor housing 102 may be formed from a suitable, optically transmissive polymer material, such as, for example, acrylic polymers (e.g., polymethylmethacrylate (PMMA)).

In some embodiments, as shown in FIG. 1, the sensor 100 may include an analyte indicator 106. In some non-limiting embodiments, the analyte indicator 106 may be a polymer graft coated, diffused, adhered, or embedded on at least a portion of the exterior surface of the sensor housing 102. The analyte indicator 106 (e.g., polymer graft) may cover the entire surface of sensor housing 102 or only one or more portions of the surface of housing 102. As an alternative to coating the analyte indicator 106 on the outer surface of sensor housing 102, the analyte indicator 106 may be disposed on the outer surface of the sensor housing 102 in other ways, such as by deposition or adhesion. In some embodiments, the analyte indicator 106 may be a fluorescent glucose indicating polymer. In one non-limiting embodiment, the polymer is biocompatible and stable, grafted onto the surface of sensor housing 102, designed to allow for the direct measurement of glucose in interstitial fluid (ISF), blood, or intraperitoneal fluid after implantation of the sensor 100. In some embodiments, the analyte indicator 106 may comprise a hydrogel.

In some embodiments, the analyte indicator 106 (e.g., polymer graft) of the sensor 100 may include indicator molecules 104. The indicator molecules 104 may be distributed throughout the entire analyte indicator 106 or only throughout one or more portions of the analyte indicator 106. The indicator molecules 104 may be fluorescent indicator molecules (e.g., TFM having the chemical name 9-[N-[6-(4,4,5,5,-tetramethyl-1,3,2-dioxaborolano)-3-(trifluoromethyl)benzyl]-N-[3-(methacrylamido)propylamino] methyl]-10-[N-[6-(4,4,5,5,-tetramethyl-1,3,2-dioxaborolano)-3-(trifluoromethyl)benzyl]-N-[2-(carboxyethyl) amino]methyl]anthracene sodium salt) or light absorbing, non-fluorescent indicator molecules. In some embodiments, the indicator molecules 104 may reversibly bind an analyte (e.g., glucose, oxygen, cardiac markers, low-density lipoprotein (LDL), high-density lipoprotein (HDL), or triglycerides). When an indicator molecule 104 has bound an analyte, the indicator molecule may become fluorescent, in which case the indicator molecule 104 is capable of absorbing (or being excited by) excitation light 329 and emitting light 331. In one non-limiting embodiment, the excitation light 329 may have a wavelength of approximately 378 nm, and the emission light 331 may have a wavelength in the range of 400 nm to 500 nm. When no analyte is bound, the indicator molecule 104 may be only weakly fluorescent.

In some embodiments, the sensor 100 may include a light source 108, which may be, for example, a light emitting diode (LED) or other light source that emits radiation, including radiation over a range of wavelengths that interact with the indicator molecules 104. In other words, the light source 108 may emit the excitation light 329 that is absorbed by the indicator molecules in the matrix layer/polymer 104. As noted above, in one non-limiting embodiment, the light source 108 may emit excitation light 329 at a wavelength of approximately 378 nm.

In some embodiments, the sensor 100 may also include one or more photodetectors (e.g., photodiodes, phototransistors, photoresistors or other photosensitive elements). For example, in the embodiment illustrated in FIG. 1, sensor 100 has a first photodetector 224 and a second photodetector 226. However, this is not required, and, in some alternative embodiments, the sensor 100 may only include the first photodetector 224. In the case of a fluorescence-based sensor, the one or more photodetectors may be sensitive to fluorescent light emitted by the indicator molecules 104 such that a signal is generated by a photodetector (e.g., photodetector 224) in response thereto that is indicative of the level of fluorescence of the indicator molecules and, thus, the amount of analyte of interest (e.g., glucose).

Some part of the excitation light 329 emitted by the light source 108 may be reflected from the analyte indicator 106 back into the sensor 100 as reflection light 333, and some part of the absorbed excitation light may be emitted as emitted (fluoresced) light 331. In one non-limiting embodiment, the emitted light 331 may have a different wavelength than the wavelength of the excitation light 329. The reflected light 333 and emitted (fluoresced) light 331 may be absorbed by the one or more photodetectors (e.g., first and second photodetectors 224 and 226) within the body of the sensor 100.

Each of the one or more photodetectors may be covered by a filter 112 (see FIG. 3) that allows only a certain subset of wavelengths of light to pass through. In some embodiments, the one or more filters 112 may be thin glass filters. In some embodiments, the one or more filters 112 may be thin film (e.g., dichroic) filters deposited on the glass and may pass only a narrow band of wavelengths and otherwise reflect most of the received light. In some embodiments, the filters may be thin film (dichroic) filters deposited directly onto the photo detectors and may pass only a narrow band of wavelengths and otherwise reflect most of the light received thereby. The filters 112 may be identical (e.g., both filters 112 may allow signals to pass) or different (e.g., one filter 112 may be a reference filter and another filter 112 may be a signal filter).

In one non-limiting embodiment, the second (reference) photodetector 226 may be covered by a reference photodiode filter that passes light at the same wavelength as is emitted from the light source 108 (e.g., 378 nm). The first (signal) photodetector 224 may detect the amount of fluoresced light 331 that is emitted from the molecules 104 in the analyte indicator 106. In one non-limiting embodiment, the peak emission of the indicator molecules 104 may occur around 435 nm, and the first photodetector 224 may be covered by a signal filter that passes light in the range of about 400 nm to 500 nm. In some embodiments, higher glucose levels/concentrations correspond to a greater amount of fluorescence of the molecules 104 in the analyte indicator 106, and, therefore, a greater number of photons striking the first photodetector 224.

In some embodiments, as shown in FIG. 1, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components, may be fabricated in the semiconductor substrate 116 with the remainder of the circuitry is secured to the semiconductor substrate 116, which may provide communication paths between the various secured components.

In some embodiments, the one or more of the sensor housing 102, analyte indicator 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

In some embodiments, the sensor 100 may include a transceiver interface device, and the transceiver 101 may include a sensor interface device. In some embodiments where the sensor 100 and transceiver 101 include an antenna or antennas (e.g., inductive elements 103 and 114), the transceiver interface device may include the inductive element 114 of the sensor 100, and the sensor interface device may include the inductive element 103 of the transceiver 101. In some of the transcutaneous embodiments where there exists a wired connection between the sensor 100 and the transceiver 101, the transceiver interface device and sensor interface device may include the wired connection.

Figure 2:
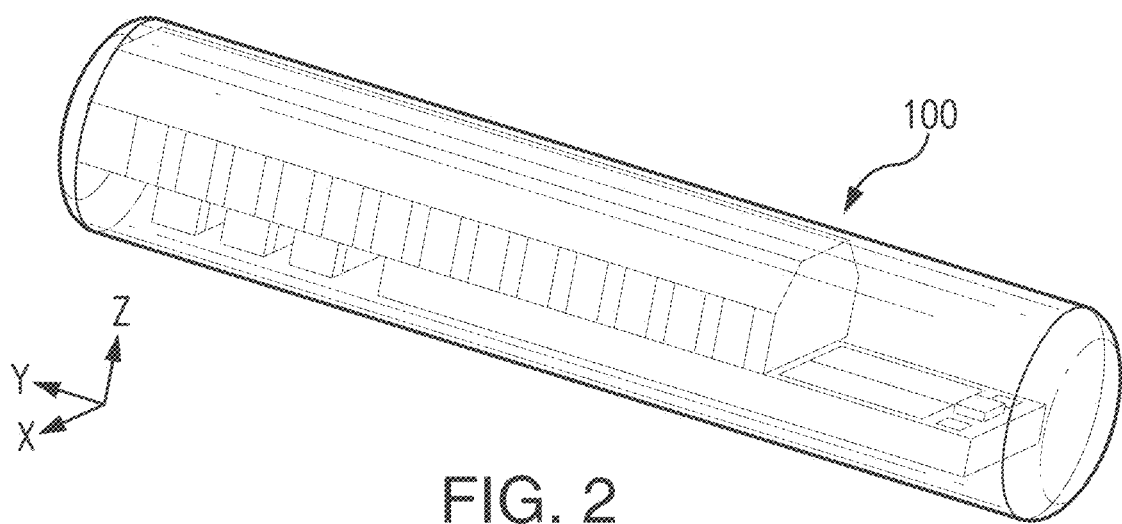
FIG. 2 illustrates a perspective view of a sensor embodying aspects of the present invention.
Figure 3:
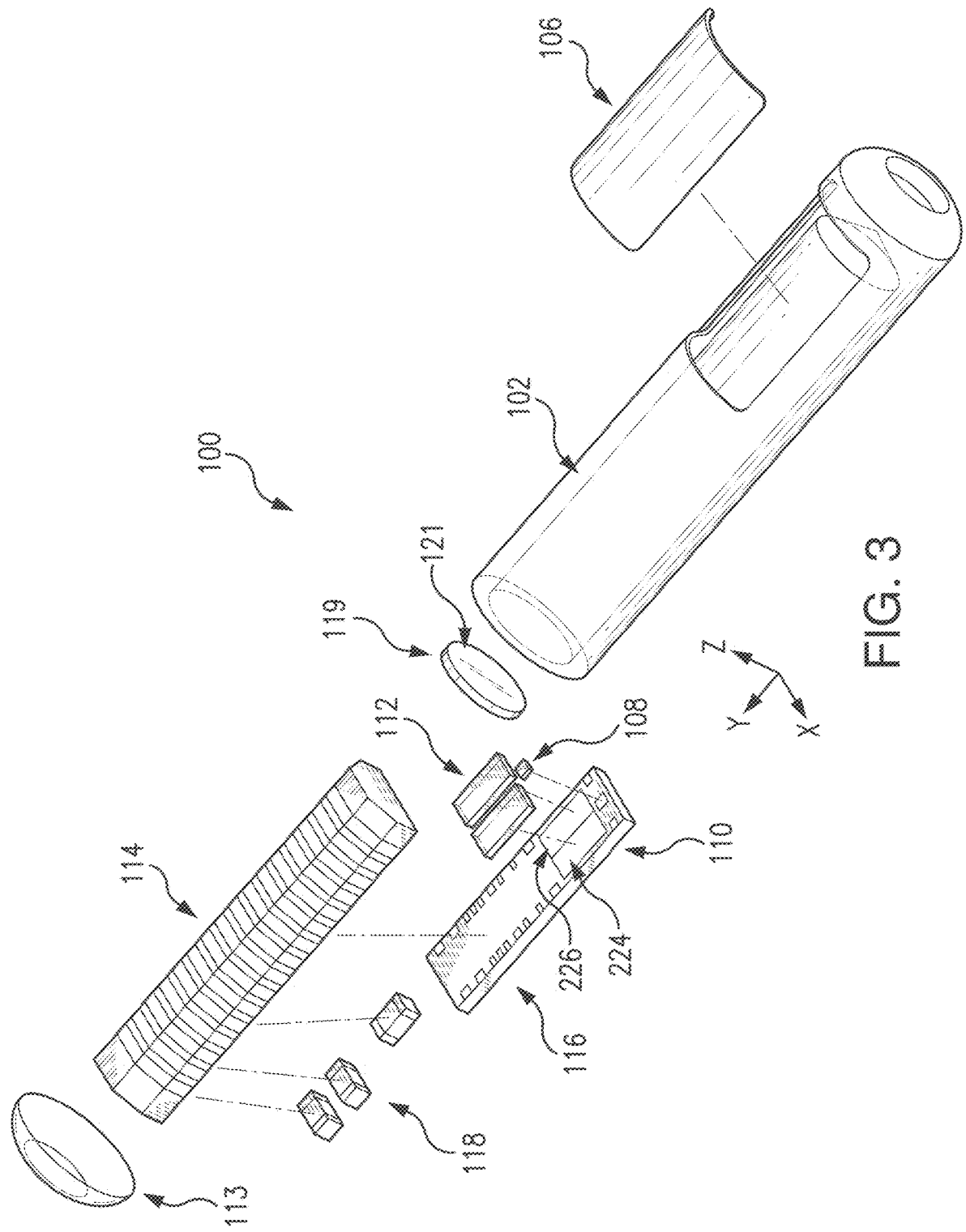
FIG. 3 illustrates an exploded view of a sensor embodying aspects of the present invention.

FIGS. 2 and 3 illustrate a non-limiting embodiment of a sensor 100 embodying aspects of the present invention that may be used in the sensor system illustrated in FIG. 1. FIGS. 2 and 3 illustrate perspective and exploded views, respectively, of the non-limiting embodiment of the sensor 100.

In some embodiments, as illustrated in FIG. 3, the sensor housing 102 may include an end cap 113. In some embodiments, the sensor 100 may include one or more capacitors 118. The one or more capacitors 118 may be, for example, one or more tuning capacitors and/or one or more regulation capacitors. The one or more capacitors 118 may be too large for fabrication in the semiconductor substrate 116 to be practical. Further, the one or more capacitors 118 may be in addition to one or more capacitors fabricated in the semiconductor substrate 116.

In some embodiments, as illustrated in FIG. 3, the sensor 100 may include a reflector 119 (i.e., mirror). Reflector 119 may be attached to the semiconductor substrate 116 at an end thereof. In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from exiting the axial end of the sensor 100.

According to one aspect of the invention, an application for which the sensor 100 was developed (although by no means the only application for which it is suitable) is measuring various biological analytes in the living body of an animal (including a human). For example, sensor 100 may be used to measure glucose, oxygen, toxins, pharmaceuticals or other drugs, hormones, and other metabolic analytes in, for example, the human body.

In some embodiments, the specific composition of the analyte indicator 106 and the indicator molecules 104 may vary depending on the particular analyte the sensor is to be used to detect and/or where the sensor is to be used to detect the analyte (e.g., in the in subcutaneous tissues, blood, or peritoneum). In some embodiments, the analyte indicator 106 facilitates exposure of the indicator molecules 104 to the analyte. In some embodiments, the indicator molecules 104 may exhibit a characteristic (e.g., emit an amount of fluorescence light) that is a function of the concentration of the specific analyte to which the indicator molecules 104 are exposed.

In some embodiments, the sensor 100 may include at least one drug eluting polymer matrix and/or a layer of catalyst and/or one or more therapeutic agents that may be provided on, adjacent to, incorporated in, or dispersed within the analyte indicator or sensor housing as described in U.S. Pat. No. 9,931,068 (Huffstetler et al.), which is incorporated herein by reference in its entirety. In some embodiments, the one or more therapeutic agents may be incorporated in the analyte indicator 106. In some embodiments, the sensor 100 may include a membrane covering at least a portion of the analyte indicator 106, and the one or more therapeutic agents may be incorporated within the membrane. In some embodiments, the one or more therapeutic agents include dexamethasone, triamcinolone, betamethasone, methylprednisolone, beclometasone, fludrocortisone, derivatives thereof, and analogs thereof, a glucocorticoid, an anti-inflammatory drug, e.g., a non-steroidal anti-inflammatory drug including but not limited to acetylsalicylic acid, isobutylphenylpropanoic acid.

Figure 4:
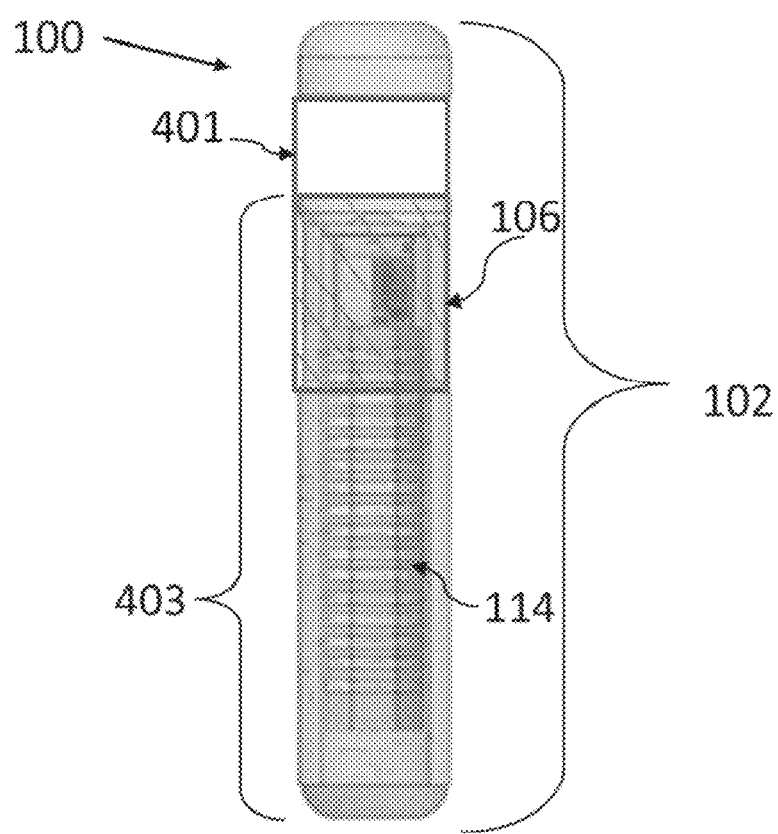
FIG. 4 is a schematic view illustrating a sensor embodying aspects of the present invention.

FIG. 4 is a schematic view of a sensor 100 embodying aspects of the present invention. In some non-limiting aspects, as shown in FIG. 4, the sensor 100 may include a drug eluting region 401 covering at least a portion of the sensor housing 102. In some non-limiting aspects, as shown in FIG. 4, the sensor 100 may include an analyte indicator 106, and the analyte indicator 106 may include a hydrogel co-polymerized with, carrying, or entrapping one or more degradative species probes of the present disclosure. In some non-limiting aspects, as shown in FIG. 4, the sensor 100 may include sensor electronic components, which may include any of the electronic components described in the present disclosure, including in FIG. 1 and FIG. 3 (e.g., the light source 108, the one or more photodetectors 110, the inductive element 114, and/or the one or more capacitors 118), as well as those described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. In some non-limiting aspects, as shown in FIG. 4, the sensor 100 may include a metal coating 403 covering at least a portion of the sensor housing 102. In some non-limiting aspects, the metal coating 403 may include one or more metals selected from Cu, W, Pt, Fe, Mo, Co, oxides, alloys, and complexes thereof. In some non-limiting aspects, the metal coating 403 may be coated on the hydrogel co-polymerized with, carrying, or entrapping one or more degradative species probes of the present disclosure.

The implantation or insertion of a medical device, such as a bio-sensor, into a user/patient's body can cause the body to exhibit adverse physiological reactions that are detrimental to the functioning of the device. The reactions may range from infections due to implantation surgery to the immunological response of a foreign object implanted in the body. That is, the performance of the implantable bio-sensor can be hindered or permanently damaged in vivo via the immunological response to an infection or the device itself. In particular, the performance of the analyte indicator 106 may be deteriorated by the immunological response of the body into which the sensor 100 is implanted. For example, as explained above, white blood cells, including neutrophils, may attack an implanted sensor 100. The neutrophils release degradative species including, inter alia, hydrogen peroxide, which may degrade indicator molecules 104 (e.g., by oxidizing a boronate group of an indicator molecule 104 and disabling the ability of the indicator molecule 104 to bind glucose). Prior to the present invention, there has been no method of identifying the degradative species that react with implanted indicator molecules. Most of the degradative species that are generated are short lived and have not been identified.

In some embodiments, the analyte indicator 106 may include one or more degradative species probes that interact or react with one or more degradative species and have distinct characteristic absorption and emission properties that can be exploited in understanding their reactivity against the corresponding degradative species generated around the sensor. In some embodiments, the one or more degradative species probes may be incorporated into the analyte indicator 106 that may cover at least a portion of the sensor housing 102. The degradative species to be detected by the one or more degradative species probes may include, but is not limited to one or more of a peroxide compound, a reactive oxygen species, a reactive nitrogen species, a free radical, enzymes, and a metal ion. In some aspects, the degradative species may include superoxide, hydrogen peroxide, hypochlorite, peroxynitrite, or a combination thereof.

In some embodiments, the one or more degradative species probes may be dispersed in, entrapped within, and/or copolymerized with the indicator molecule 104. In some embodiments, the one or more degradative species probes may be provided in the analyte indicator 106 (e.g., polymer graft or hydrogel). In some embodiments, the one or more degradative species probes may interact and/or react with degradative species and exhibit distinct characteristic absorption and emission properties as a result of the interaction and/or reaction. In some embodiments, the one or more degradative species probes are selective against specific degradative species. In some embodiments, the absorption and emission properties of the degradative species probes are detectable and quantifiable. In some embodiments, the detected absorption and emission properties of the degradative species probes are indicative of the identity of one or more degradative species. In some embodiments, the detected absorption and emission properties of the degradative species probes are indicative of the quantity of one or more degradative species.

In some embodiments, the one or more degradative species probes may sequester, neutralize the degradative species and/or inhibit activity thereof. In some embodiments, the one or more degradative species probes may bind to the degradative species. In some embodiments, the one or more degradative species probes may sequester the degradative species so as to inhibit, reduce, and/or prevent degradation of the analyte indicator by the degradative species. Accordingly, in some embodiments, the one or more degradative species probes reduce degradation of the analyte indicator 106.

In some non-limiting embodiments, the one or more degradative species probes may be one or more fluorescent probes. In one non-limiting embodiment, the one or more degradative species probes may utilize a boronate de-protection mechanism to provide high selectivity and optical dynamic range for detecting specific degradative species. For example, in some embodiments, a degradative species probe may be utilized that is highly selective for detecting hydrogen peroxide over superoxide, nitric oxide, tert-butyl hydroperoxide, hypochlorite, singlet oxygen, ozone, and/or hydroxyl radical. In some embodiments, the one or more degradative species probes are water-soluble systems that respond to specific degradative species selectively over other degradative species in vivo. In some embodiments, the one or more degradative species probes have low reactivity with thiols that are present in high concentrations within cells and do not require an external activating enzyme.

In some non-limiting embodiments, the one or more degradative species probes may be one or more of the following compounds:

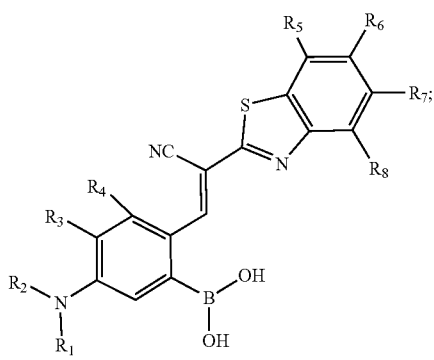

(Formula I)

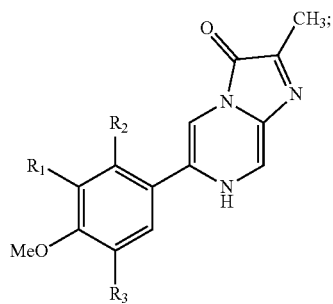

(Formula II)

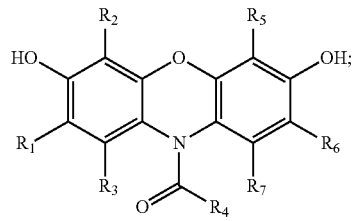

(Formula III)

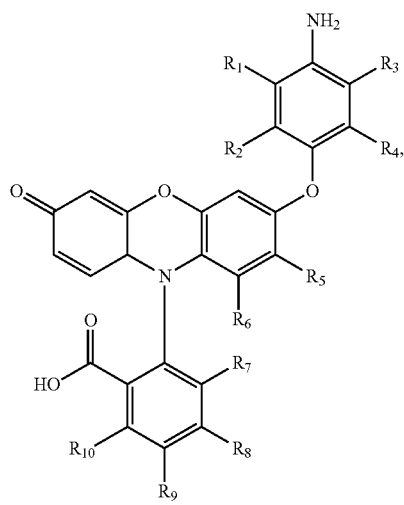

(Formula IV)

wherein each R1, R2, R3, R4, R5, R6, R7, R8, R9, R10, and R6 is independently selected from H, C1-C20 alkyl, C1-C20 alkoxy, carboxy, aryl, heteroaryl, polycyclic, alkoxy, halide, SH, aryloxy, alkylthio, amino, substituted amino, alkoxycarbonyl, alkanoylamido, aroylamido, heterocyclocarbonylamido, heteroaroylamido, alkanoyl(alkylsubstituted)amido, aroyl(alkylsubstituted)amido, heteroaroyl(alkylsubstituted)amido, and heterocyclocarbonyl(alkylsubstituted)amido, and formulae I-VIII may be optionally substituted with C1-5 alkyl, alkoxy, cyano, halo and/or trifluoromethyl at any position;

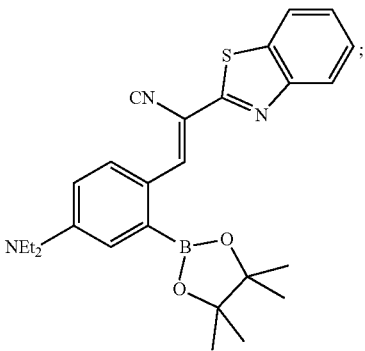

(Formula V)

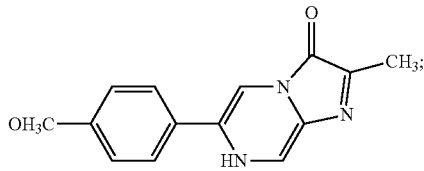

(Formula VI)

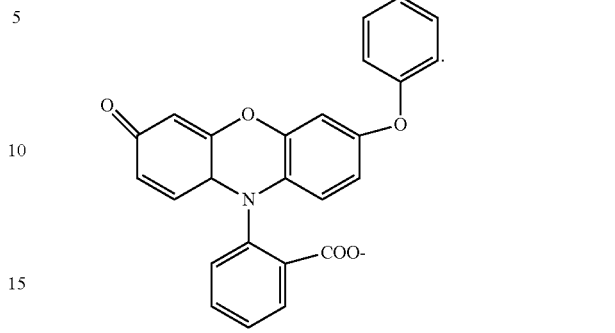

(Formula VIII)

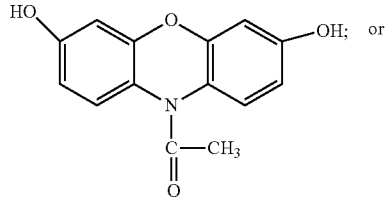

(Formula VII)

The present disclosure involves the use of compounds that trap or otherwise react with reactive oxygen species. In some aspects, compounds of Table 1 below and Formulae I-VIII are used according to the present disclosure. Each of the references cited in Table 1, and each of the detection reagents listed in Table 1 and disclosed in the cited references is incorporated herein by reference in its entirety. It is an object of the present disclosure to use probes that react with particular degradative species selectively over other degradative species so as to identify specific degradative species that come into contact with a given sensor 100 when it is implanted in a subject.

TABLE 1

| Reactive Oxygen Species (Structure) | Detection Reagents | |
|---|---|---|
| Hydrogen peroxide ($H_2O_2$) | Carboxy-$H_2$DCFDA (C400)[1-3] <br> CM-$H_2$DCFD (C6827)[4,5] <br> Dihydrocalcein AM (D23805) <br> Dihydrorhodamine 123 (D632, D23806)[6] <br> Dihydrorhodamine 6G (D633)[7] | $H_2$DCFDA (C399)[8-11] <br> Lucigenin (L6868)[12,13] <br> Luminol (L8455)[14] <br> RedoxSensor™ Red CC-1 (R14060)[15] |
| Hydroxyl radical* (HO•) | 3'-(p-Aminophenyl) fluorescein (APF, A36003) <br> 3'-(p-Aminophenyl) fluorescein (HPF, H36004) | Proxyl fluorescamine (C7924)[17] <br> TEMPO-9-AC (A7923) <br> CM-$H_2$DCFDA (C6827)[16] |
| Hypochlorous acid (HOCl) | Aminophenyl fluorescein (APF, A36003) | Luminol (L8455)[19-21] <br> Dihydrorhodamine 123 (D632, D23806)[18] |
| Nitric oxide (NO) | DAF-FM (D23841)[22,23] <br> DAF-FM diacetate (D23842, D23844)[22,23] | 2,3-Diaminonaphthalene (D7918) <br> Luminol (L8455)[24] <br> DAA (D23840)[25] |
| Peroxyl radical, including both alkylperoxyl and hydroperoxyl radicals, wherein R = H (ROO•) | BODIPY® FL EDA (D23841)[27] <br> BODIPY® 665/676 (B3932)[28] <br> $H_2$DCFDA (C399)[29-33] <br> Carboxy-$H_2$DCFDA (C400)[34] <br> CM-$H_2$DCFDA (C6827) | DPPP (D77894)[35-37] <br> Luminol (L8455)[38-40] <br> cis-Parinaric acid (P36005)[41,42] <br> RedoxSensor™ Red CC-1 (R14060)[15] |
| Peroxynitrite anion † (ONOO)) | 3'-(p-Aminophenyl) fluorescein (APF, A36003) <br> 3'-(p-Aminophenyl) fluorescein (HPF, H36004) <br> $H_2$DCFDA (C399)[43,44] <br> Carboxy-$H_2$DCFDA (C400) | Coelenterazine (C2944)[45] <br> Dihydrorhodamine 123 (D632, D23806)[43,46-48] <br> Dihydrorhodamine 6G (D633) <br> Luminol (L8455)[43,49-50] <br> CM—$H_2$DCFDA (C6827) |
| Singlet oxygen ‡ ($^1O_2$) | Singlet Oxygen Sensor Green reagent (536002) | trans-1-(2'-methoxyvinyl) pyrene (M7913)[51,52] |
| Superoxide anion (•$O_2$) | Coelenterazine (C2944)[53,54] <br> Dihydroethidium (D1168, D11347, D23107)[55,56] <br> Fc OxyBurst® Green assay reagent (F2902)[57,58] | MCLA (M23800)[65,66] <br> MTT (M6494)[67] <br> NBT (N6495)[68] <br> RedoxSensor™ Red CC-1 (R14060)[15] |

TABLE 1-continued

| Reactive Oxygen Species (Structure) | Detection Reagents | |
|---|---|---|
| | OxyBurst ® Green H$_2$DCFDA SE (D2935)[59,60] | TEMPO-9-AC (A7923) XTT (X6493)[69] |
| | OxyBurst ® Green H$_2$HFF BSA (O13291)[61] | Lucigenin (L6868)[62,63] Luminol (L8455)[64] |

*Hydroxyl radicals can also be photosensitized by malachite green isothiocyanate (M689) or generated by a N-(1,10-phenanthrolin-5-yl)iodoacetamide (P6879) metal-ligand complex.
† 3-Nitrotyrosine, a product of this potent nitrating reagent, can be detected with an anti-nitrotyrosine antibody (A21285).
‡ Singlet oxygen can also be photosensitized by hypericin (H7476), rose Bengal diacetate (R14000) and merocyanine 540 (M24571).
[1]Biol Pharm Bull (2000) 23:1153;
[2]J Neuosci (1999) 19:9209;
[3]J Biol Chem (1996) 271:21505;
[4]J Biol Chem (2001) 276:21938;
[5]Proc Natl Acad Sci U S A (1997) 94:11557;
[6]Biochim Biophys Acta (1999) 1454:275;
[7]Proc Natl Acad Sci U S A (2000) 97:8266;
[8]J Biol Chem (2001) 276:514;
[9]J Immunol Methods (1989) 117:53;
[10]Brain Res (1994) 635:113;
[11]J Biol Chem (1999) 274:37111;
[12]Analyst (1986) 3:941;
[13]J Am Chem Soc (1979) 101:5347;
[14]J Bone Miner Res (1992) 7:1139;
[15]Free Radic Biol Med (2000) 28:1266;
[16]Proc Natl Acad Sci U S A (2001) 98:1643;
[17]Anal Chem (1997) 69:4295;
[18]Nitric Oxide (1997) 1:145;
[19]Biochem Biophys Acta 1991) 1097:145;
[20]Luminescence (1999) 14:239;
[21]Am J Physiol (1989) 257.C347;
[33]Methods Enzymol (1984) 105:352;
[34]J Biol Chem (1998) 273:5294;
[35]J Chromatogr (1993) 628:31;
[36]Anal Lett (1987) 20:731;
[37]Methods Enzymol (1990) 186:157;
[38]Free Radic Biol Med (1995) 18:1;
[39]Biomed Chromatogr (1990) 4:131;
[40]Lipids (1998) 33:1235;
[41]J Biol Chem (1997) 272.12328;
[42]Biochem Biophys Res Commun (1998) 244:647;
[43]Free Radic Biol Med (2001) 30:463;
[44]FEBS Lett (2000) 468:89;
[45]Circ Res (1999) 84:1203;
[46]FASEB J 2001;
[47]Arch Biochem Biophys (2000) 373:302;
[48]FASEB J (2000) 14:1061;
[49]J Biol Chem (1996) 271:29223;
[50]Arch Biochem Biophys (1994) 310:352;
[51]Biochem Biohys Res Commun (1984) 123:869;
[52]Methods Enzymol (1986) 133:569;
[53]Anal Biochem (1992) 206:273;
[54]Free Radic Biol Med (2000) 29:170;
[55]Circ Res (2001) 88:824;
[56]J Biol Chem (2001) 276:17621;
[57]J Leukoc Biol (1997) 62:329;
[58]J Biol Chem (1995) 270:8328;
[59]Immunology (1994) 83:507;
60J Immunol Methods (1990) 130:223;
[61]Biophys J (1998) 75:2577;
[62]Free Radic Biol Med (2000) 28:1232;
[63]J Biol Chem (1998) 273:2015;
[64]J Immunol Methods (1992) 155:151;
[65]Free Radic Res (2000) 32:265;
[66]Anal Biochem (1999) 271:53;
[67]Fee Radic Res Commun (1993) 18:369;
[68]Arch Biochem Biophys (1997) 342:275;
[69]Plant Physiol (1998) 117:491.

In some non-limiting embodiments, a sensor 100 for measurement of an analyte (e.g., glucose) in a medium (e.g., interstitial fluid) within a living animal (e.g., a human) contains one or more of the following components: a sensor housing 102; a light source 108 within the sensor housing 102 configured to emit excitation light 329; an analyte indicator 106 covering a portion of the sensor housing 102, one or more indicator molecules 104 that are part of the analyte indicator 106, reversibly bind the analyte, are positioned to be irradiated by the excitation light, and are configured to emit light 331 indicative of the amount of the analyte in the medium within the living animal; a photodetector 224 within the sensor housing 102 that is sensitive to light 331 emitted by the one or more indicator molecules 104 and configured to generate a signal indicative of the amount of the analyte in the medium within the living animal; and one or more compounds of Formulae I-VIII to selectively interact or react with degradative species. In some non-limiting embodiments, the sensor 100 may include one or more degradative species probes, e.g., compounds of Formulae I-VIII, that are positioned to be irradiated by excitation light, and are configured to emit light indicative of the amount of the degradative species in the medium within the living animal. In some non-limiting embodiments, the compounds of Formulae I-VIII are irradiated by excitation light after explanation of the sensor for in vitro analysis. In such non-limiting embodiments, an excitation light source outside of the sensor can be used for excitation of the compounds of Formulae I-VIII. In some non-limiting embodiments, the sensor 100 may include a drug eluting region 401, e.g., a drug eluting matrix, collar, and/or a layer of catalyst provided on, adjacent to, or incorporated in the analyte indicator 106.

Figure 5:
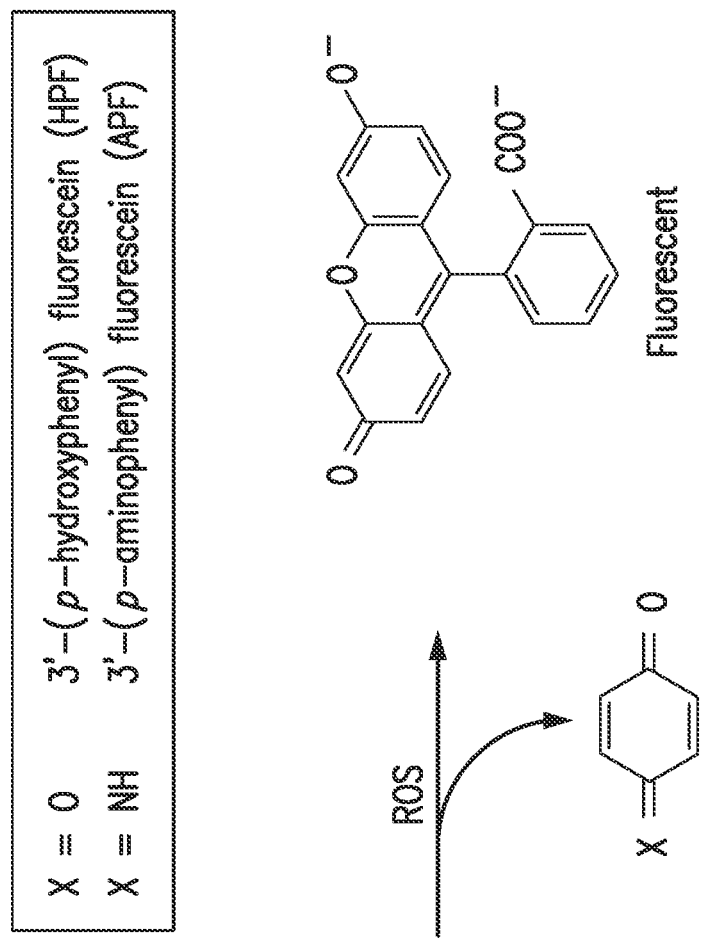
FIG. 5 shows an exemplary reaction scheme for the compound of Formula VIII ("APF").
Figure 5:
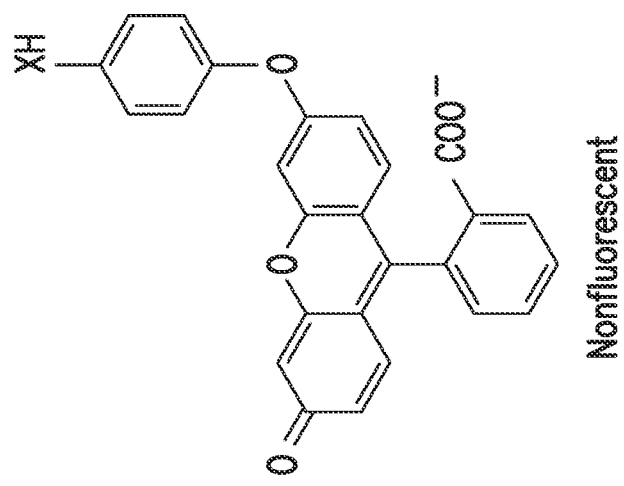

In some non-limiting embodiments, each of the one or more degradative species probes may be selective for one or more degradative species over other degradative species as exemplified in Table 1. For example, in some embodiments, the compounds of Formulae I and V may be peroxynitrite-selective. In some embodiments, the compounds of Formulae II and VI may be superoxide-selective. In some embodiments, the compounds of formulae III and VII may be hydrogen peroxide-selective. In some embodiments, compounds of Formulae IV and VIII may be hypochlorite- and peroxynitrite-selective. An exemplary reaction scheme and reactivity quantification for the compound of Formula VIII ("APF") is shown in FIG. 5 and in Table 2 below.

In some embodiments, each of the one or more degradative species probes may undergo a specific change in its emission profile upon reacting with degradative species that allow detection, identification, and quantification of degradative species in the environment of the sensor 100. For example, in some embodiments, a compound of formulae I-VIII may be essentially non-fluorescent in the absence of degradative species and, upon reaction with a degradative species, become strongly fluorescent. The emission profile of each probe demonstrates selectivity for specific degradative species, thereby allowing identification of the degradative species in the vicinity of the sensor 100.

As a non-limiting example, the following reaction illustrates a non-limiting embodiment useful according to the present disclosure:

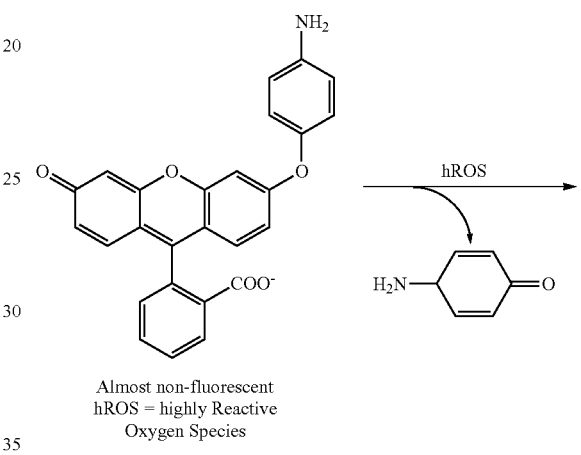

Almost non-fluorescent
hROS = highly Reactive Oxygen Species

TABLE 2

| Reactive Oxygen Species (ROS) | ROS Generation Method | APF* | HPF* | H₂DCFDA* |
|---|---|---|---|---|
| Hydrogen peroxide (H₂O₂) | 100 μM H₂O₂ | <1 | 2 | 190 |
| Hydroxyl radical (HO·) | 100 μM ferrous perchlorate (II) and 1 mM of H₂O₂ | 1200 | 730 | 7400 |
| Hypochlorite anion (⁻OCl) | 3 μM (final) ⁻OCl | 3600 | 6 | 86 |
| Nitric oxide (NO) | 100 μM 1-hydroxy-2-oxo-3-(3-aminopropyl)-3-methyl-1-triazene (NOC-7) | <1 | 6 | 150 |
| Peroxyl radical (ROO•) | 100 μM 2,2'-azobis(2-amidinopropane), dihydrochloride (AAPH) | 2 | 17 | 710 |
| Peroxynitrite anion (ONOO⁻) | 3 μM (final) ONOO | 560 | 120 | 6600 |
| Singlet oxygen (¹O₂) | 100 μM 3-(1,4-dihydro-1,4-epidioxy-1-napthyl) propionic acid | 9 | 5 | 26 |
| Superoxide anion (•O₂⁻) | 100 μM KO₂ | 6 | 8 | 67 |
| Autooxidation | 2.5 hours exposure to fluorescent light source | <1 | <1 | 2000 |

*10 μm of APF, HPF, or DCF (2',7'-dichlorofluorescein) were added to sodium phosphate buffer (0.1M, pH 7.4); ROS were generated as indicated; and fluorescence was measured using excitation/emission wavelengths of 490/515 nm (for APF and HPF) or 500/520 nm (for DCF). DCF was obtained by hydrolysis of H₂DCFDA with base as described in J Biol Chem (2003) 278:3170; dyhydrofluorescein diacetates are colorless and nonfluorescent until both of the acetate groups are hydrolyzed and the products are subsequently oxidized to fluorescein derivatives.

-continued

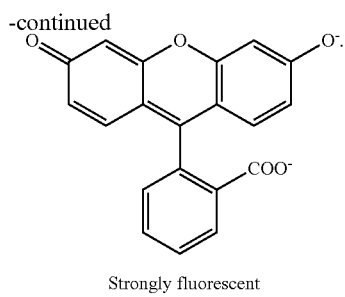

Strongly fluorescent

In some non-limiting embodiments, the one or more compounds of Formulae I-VIII may be provided in the analyte indicator 106 (e.g., hydrogel) of the analyte sensor 100. In some non-limiting embodiments, one or more compounds of Formulae I-VIII may be incorporated into the analyte indicator 106 by polymerizing the one or more compounds of Formulae I-VIII as a co-monomer with indicator monomer and one or more acrylate monomers. In some non-limiting embodiments, one or more compounds of Formulae I-VIII may be provided as co-monomers of four monomers according to Formula IX: A-B-C-D [Formula IX], wherein A is an indicator monomer, B is a methacrylate monomer, C is a polyethylene glycol monomer, and D is a compound of one or more of Formulae I-VIII monomer, wherein A is 0.001 to 10% by weight, B is 1 to 99% by weight, C is 1 to 99% by weight, and D is 0.001 to 99% by weight of the total polymer. In some aspects, A is 0.01 to 10% by weight, B is 1 to 99% by weight, C is 1 to 99% by weight, and D is 0.01 to 99% by weight of the total polymer.

In some non-limiting embodiments, the analyte indicator 106 may contain four monomers: (i) the TFM fluorescent indicator, (ii) hydroxyethylmethacrylate (HEMA), which is a methacrylate, (iii) polyethylene glycol (PEG), and (iv) a compound of Formulae I-VIII. In some embodiments, the PEG may be polyethylene glycol methacrylate (PEG-methacrylate) or polyethylene glycol diacrylate (PEG-diacrylate or PEGDA), and the one or more compounds of Formulae I-VIII may be two or more of compounds of Formula I-VIII. In some embodiments, the four monomers may be in specific molar ratios. For example, in some non-limiting embodiments in which the analyte indicator 106 is opaque, the analyte indicator 106 may comprise 0.001 to 10 molar percent, HEMA may comprise 10 to 90 molar percent, PEGDA may comprise 10 to 90 molar percent, and the compound of Formula I or a compound of Formula III may comprise 0.001 to 90 molar percent. With this formulation, the combined (i.e., total) monomers may, in one example, be 30% by volume of the polymerization solution used for the polymerization reaction with the remainder of the polymerization solution being water (i.e., the polymerization solution may be 70% water by volume). For another example, in one non-limiting embodiment, the analyte indicator 106 may be made using a polymer solution that is 50% water by volume and 50% monomers by volume.

In some embodiments, the relative molar percent of the compound of Formulae I-VIII may be within a specific range. In some embodiments, the relative molar percent of the compound of one or more of Formulae I-VIII ranges between 0.1 and 100 molar percent. If the relative molar percent of the compound of one or more of Formulae I-VIII is greater than this range, the hydrogel is not formed. If the relative molar percent of the compound of one or more of Formulae I-VIII is lower than this range, the unexpected longevity and functionality-boosting effects described in this disclosure may not obtained.

In some embodiments, the PEGDA may act as a cross-linker and create a sponge-like matrix/hydrogel. In some non-limiting embodiments, the PEG-containing graft/hydrogel may become clear if a sufficient amount of additional PEG is added to the mixture (i.e., if it is fabricated with a higher concentration of PEG), and a clear analyte indicator 106 may be made from such a formulation. For example, in one non-limiting embodiment, the polymer graft 106 may be made using a polymer solution that is 50-60% water by volume and 40-50% monomers by volume, where the TFM fluorescent indicator, HEMA, PEG-methacrylate, and one or more compounds of Formulae I-VIII may comprise 0.01 to 10%, 1 to 99%, 1 to 99%, and 0.01 to 99% by weight, of the monomers in the solution. In some embodiments, the polymer graft may be synthesized using conventional free radical polymerization.

In some instances, the amount of the one or more compounds of Formulae I-VIII incorporated into the analyte indicator 106 is between about 0.1 mg and 5 mg, about 0.2 mg and 4 mg, about 0.5 mg and 3 mg, about 1 mg and 2.5 mg, about 1.5 mg and 2 mg, about 2 mg to 2.4 mg, including all iterations of weights within the specified ranges.

In some instances, sensors loaded with one or more compounds of Formulae I-VIII reduce oxidation of analyte indicator molecules by degradative species including superoxide, hydrogen peroxide, hypochlorite, and peroxynitrite.

In some embodiments, the sensor 100 may additionally include a series of dyes that may be entrapped or co-polymerized onto the hydrogel and implanted into animal models. Sensors 100 implanted into animal models may be explanted at defined time intervals and characterized for changes to absorption/emission properties, thereby confirming and quantifying reactivity with degradative species. In some embodiments, changes in signal intensities may be compared to quantitate the relative amounts in which different degradative species detected by the different probes are generated. In some embodiments, a mixture of dyes may be used. In some embodiments, the change in the relative signals of the mixture of dyes upon reaction with degradative species may allow one to determine the relative ratios in which the degradative species have been generated. For example, the relative ratio of one or two (or more) specific degradative species to all other degradative species may be determined by using a mixture of dyes, each of which is specific for a particular degradative species.

Some embodiments of the present disclosure may include methods of identifying the relative amounts and/or identities of degradative species that are generated in vivo upon implantation of a sensor 100. Some embodiments may include implanting a sensor according to the present disclosure and detecting changes in absorption and/or emission profiles of one or more degradative species probes that form a part of the implanted sensor 100.

Some embodiments of the present disclosure may include methods of screening compounds to determine which compounds are useful for inhibiting or neutralizing the activity of specific degradative species. Some embodiments of the present disclosure may include methods of screening compounds to determine which compounds are causative of increased generation of degradative species. Some embodiments of the present disclosure may include methods of screening compounds to determine which compounds are causative of decreased generation of degradative species. Some embodiments of the present disclosure may include a method of detecting and quantifying performance measures of an implantable sensor after modification of the implantable sensor. In some embodiments, the method may include modifying the sensor 100 to incorporate one or more additional materials in the sensor that are believed to improve performance or longevity thereof, implanting the modified sensor into an animal, and using the degradative species probes and/or dyes of the present disclosure to detect changes in absorption and/or emission profiles of one or more degradative species probes or dyes that form a part of the modified implanted sensor. In some embodiments, the method may include modifying the sensor 100 to replace one or more materials with one or more new materials that are believed to improve performance or longevity thereof, implanting the modified sensor into an animal, and using the degradative species probes and/or dyes of the present disclosure to detect changes in absorption and/or emission profiles of one or more degradative species probes or dyes that form a part of the modified implanted sensor.

In some embodiments, the method may include modifying the sensor 100 to incorporate one or more additional materials in the sensor that are believed to improve performance or longevity thereof, subjecting the modified sensor to an in vitro performance test, and using the degradative species probes and/or dyes of the present disclosure to detect changes in absorption and/or emission profiles of one or more degradative species probes or dyes that form a part of the modified implanted sensor. In some embodiments, the method may include modifying the sensor 100 to replace one or more materials with one or more new materials that are believed to improve performance or longevity thereof, subjecting the modified sensor to an in vitro performance test, and using the degradative species probes and/or dyes of the present disclosure to detect changes in absorption and/or emission profiles of one or more degradative species probes or dyes that form a part of the modified implanted sensor.

Figure 6:
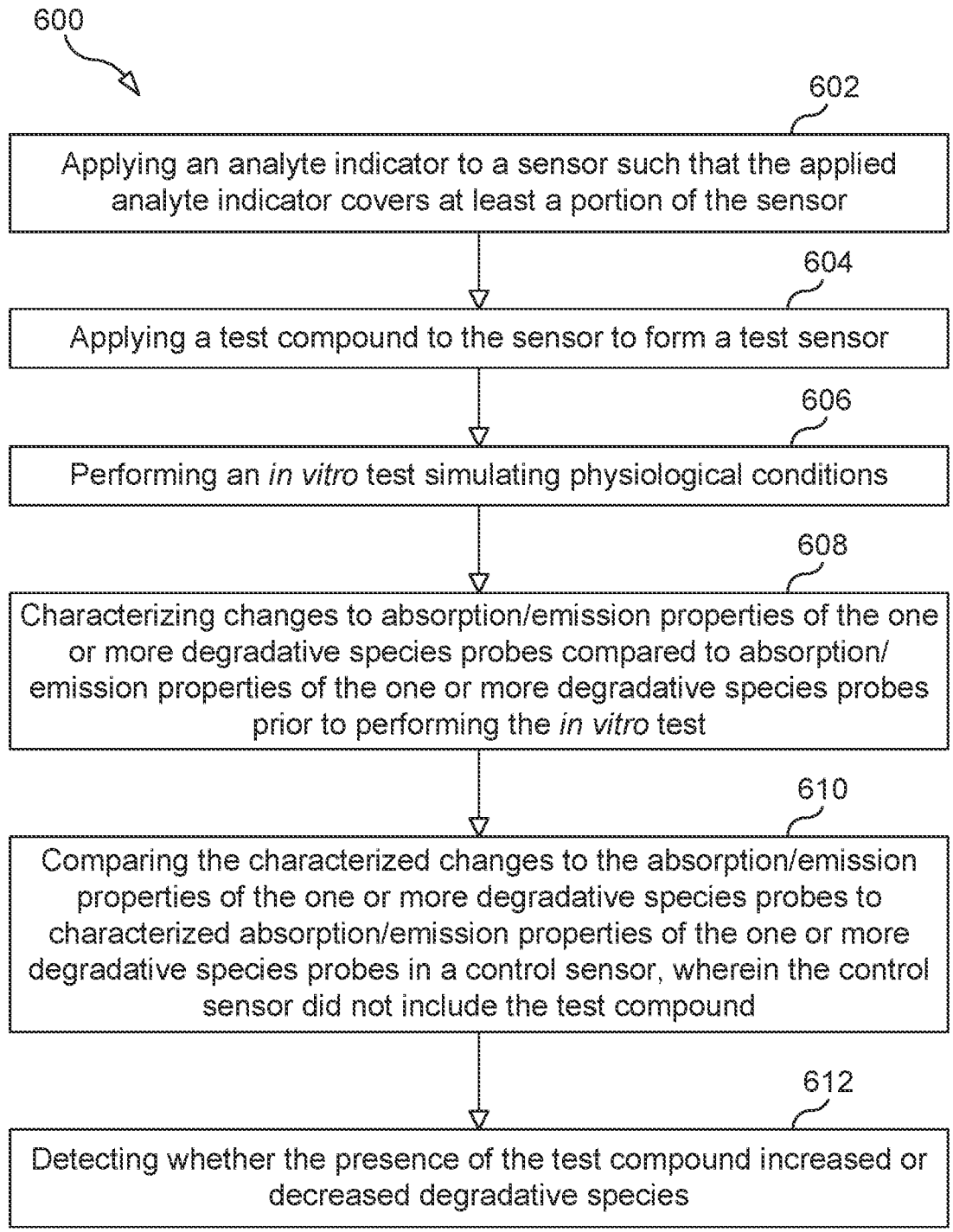
FIG. 6 illustrates steps of a method of screening compounds for inclusion in an implantable sensor according to some embodiments of the present disclosure.

FIG. 6 is a flow chart illustrating a process 600 of screening compounds for inclusion in an implantable sensor 100 embodying aspects of the present invention. In some embodiments, the process 600 may include a step 602 of applying an analyte indicator 106 to a sensor 100 such that the applied analyte indicator 106 covers at least a portion of the sensor 100. In some embodiments, the analyte indicator 106 may include one or more degradative species probes. In some embodiments, the degradative species probes may have absorption and/or emission profiles that are selective for a specific degradative species. In some embodiments, the process 600 may include a step 604 of applying a test compound to the sensor to form a test sensor. In some embodiments, the process 600 may include a step 606 of performing an in vitro test simulating physiological conditions for a defined time period. In some embodiments, the process 600 may include a step 608 of characterizing changes to absorption/emission properties of the one or more degradative species probes compared to absorption/emission properties of the one or more degradative species probes prior to performing the in vitro test. In some embodiments, the process 600 may include a step 610 of comparing the characterized changes to the absorption/emission properties of the one or more degradative species probes to characterized absorption/emission properties of the one or more degradative species probes in a control sensor. In some embodiments, the control sensor did not include the test compound. In some embodiments, the process 600 may include a step 612 of detecting whether presence the test compound increased or decreased degradative species.

Figure 7:
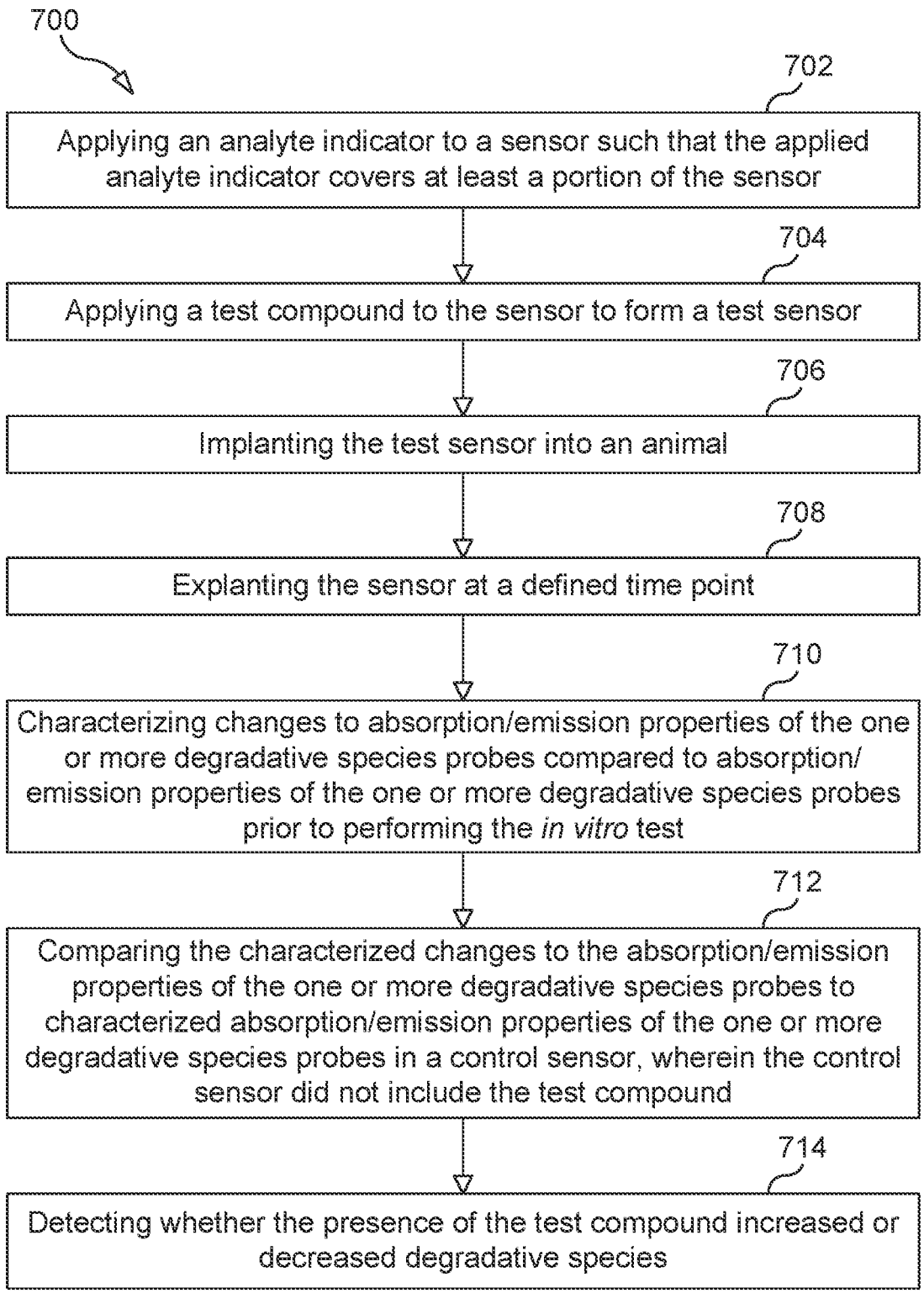
FIG. 7 illustrates steps of a method of screening compounds for inclusion in an implantable sensor according to some embodiments of the present disclosure.

FIG. 7 is a flow chart illustrating a process 700 of screening compounds for inclusion in an implantable sensor 100 embodying aspects of the present invention. In some embodiments, the process 700 may include a step 702 of applying an analyte indicator 106 to a sensor 100 such that the applied analyte indicator 106 covers at least a portion of the sensor 100. In some embodiments, the analyte indicator 106 may include one or more degradative species probes. In some embodiments, the degradative species probes may have absorption and/or emission profiles that are selective for a specific degradative species. In some embodiments, the process 700 may include a step 704 of applying a test compound to the sensor to form a test sensor. In some embodiments, the process 700 may include a step 706 of implanting the test sensor into an animal. In some embodiments, the process 700 may include a step 708 of explanting the sensor at a defined time point. In some embodiments, the process 700 may include a step 710 of characterizing changes to absorption/emission properties of the one or more degradative species probes compared to absorption/emission properties of the one or more degradative species probes prior to implanting. In some embodiments, the process 700 may include a step 712 of comparing the characterized changes to the absorption/emission properties of the one or more degradative species probes to characterized absorption/emission properties of the one or more degradative species probes in a control sensor. In some embodiments, the control sensor did not include the test compound. In some embodiments, the process 700 may include a step 714 of detecting whether presence the test compound increased or decreased degradative species in an in vivo environment of the implantable sensor.

Figure 8:
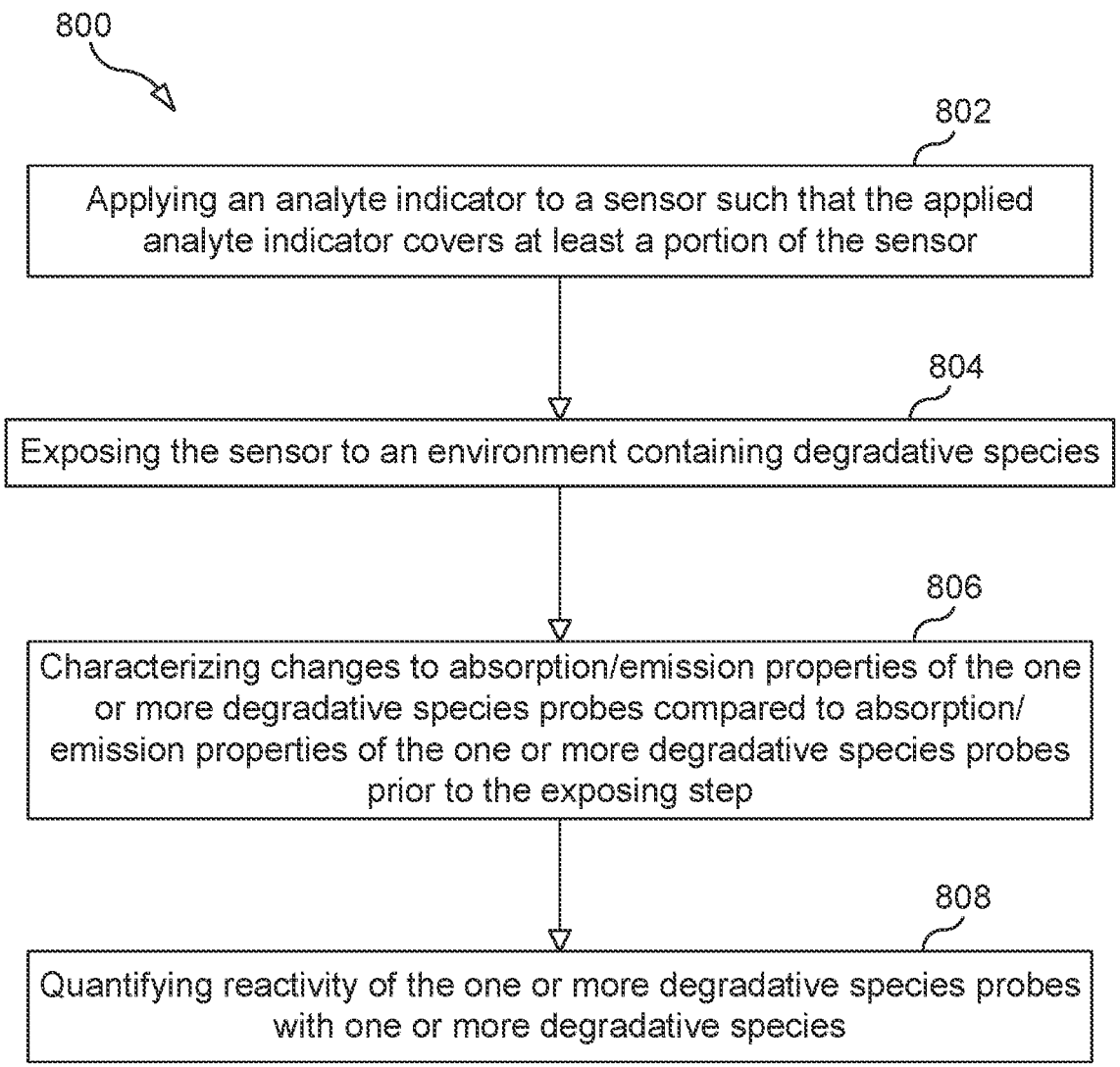
FIG. 8 illustrates steps of a method of identifying and/or quantifying degradative species in an environment of a medical device according to some embodiments of the present disclosure.

FIG. 8 is a flow chart illustrating a process 800 of identifying and/or quantifying degradative species in an environment of a medical device embodying aspects of the present invention. In some embodiments, the process 800 may include a step 802 of applying an analyte indicator 106 to a sensor 100 such that the applied analyte indicator 106 covers at least a portion of the sensor 100. In some embodiments, the analyte indicator 106 may include one or more degradative species probes. In some embodiments, the degradative species probes may have absorption and/or emission profiles that are selective for a specific degradative species. In some embodiments, the process 800 may include a step 804 of exposing the sensor to an environment containing degradative species. In some embodiments, the process 800 may include a step 806 of characterizing changes to absorption/emission properties of the one or more degradative species probes compared to absorption/emission properties of the one or more degradative species probes prior to the exposing step. In some embodiments, the process 800 may include a step 808 of quantifying reactivity of the one or more degradative species probes with one or more degradative species.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although in some embodiments, the analyte sensor 100 may be an optical sensor, this is not required, and, in one or more alternative embodiments, the analyte sensor may be a different type of analyte sensor, such as, for example, an electrochemical sensor, a diffusion sensor, or a pressure sensor. Also, although in some embodiments, the analyte sensor 100 may be an implantable sensor, this is not required, and, in some alternative embodiments, the analyte sensor may be a transcutaneous sensor having a wired connection to an external transceiver. For example, in some alternative embodiments, the analyte sensor 100 may be located in or on a transcutaneous needle (e.g., at the tip thereof). In these embodiments, instead of wirelessly communication using an antenna (e.g., inductive element 114), the analyte sensor may communicate with the external transceiver using one or more wires connected between the external transceiver and a transceiver transcutaneous needle including the analyte sensor. For another example, in some alternative embodiments, the analyte sensor may be located in a catheter (e.g., for intravenous blood glucose monitoring) and may communicate (wirelessly or using wires) with an external transceiver.

What is claimed is:

1. A sensor for measurement of an analyte in a medium within a living animal, the sensor comprising:
   an analyte indicator; and
   one or more degradative species probes having absorption and/or emission profiles that are selective for a specific degradative species, wherein the one or more degradative species probes comprise:
   (a) a degradative species probe of Formula I:

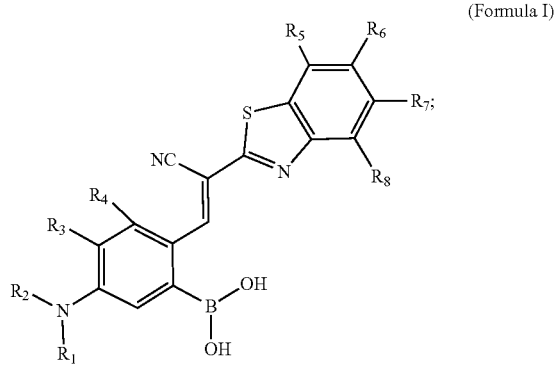

(Formula I)

(b) a degradative species probe of Formula II:

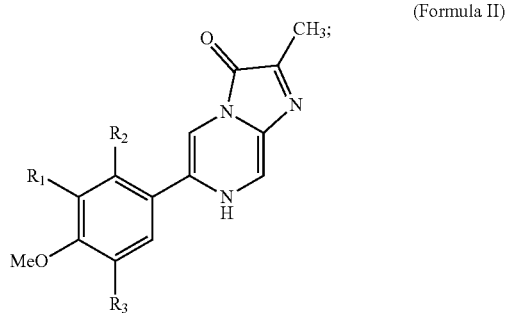

(Formula II)

(c) a degradative species probe of Formula IV:

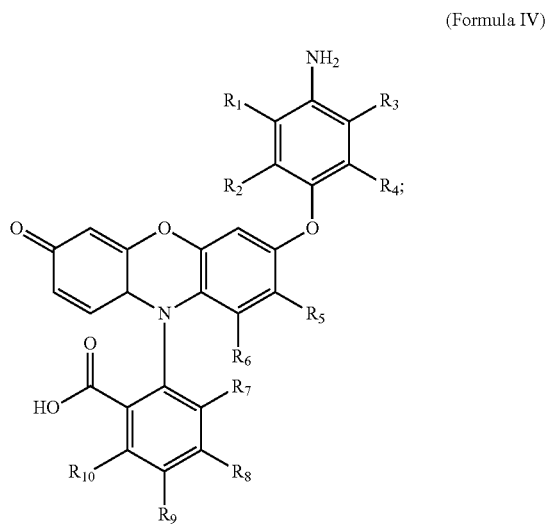

(Formula IV)

(d) the degradative species probe of the Formula I and the degradative species probe of the Formula II;
   (e) the degradative species probe of the Formula II and the degradative species probe of the Formula IV;
   (f) the degradative species probe of the Formula I and the degradative species probe of the Formula IV; or
   (g) the degradative species probe of the Formula I, the degradative species probe of the Formula II, and the degradative species probe of the Formula IV,
   wherein each R1, R2, R3, R4, R5, R6, R7, R8, R9, and R10 is independently selected from the group consisting of H, C1-C20 alkyl, C1-C20 alkoxy, carboxy, aryl, heteroaryl, polycyclic, alkoxy, halide, SH, aryloxy, alkylthio, amino, substituted amino, alkoxycarbonyl, alkanoylamido, aroylamido, heterocyclocarbonylamido, heteroaroylamido, alkanoyl(alkylsubstituted) amido, aroyl(alkylsubstituted)amido, heteroaroyl(alkylsubstituted)amido, and heterocyclocarbonyl(alkyl substituted)amido.

2. The sensor of claim 1, further comprising a sensor housing, wherein the analyte indicator covers at least a portion of the sensor housing.

3. The sensor of claim 1, further comprising a sensor substrate or sensor electrode, wherein the analyte indicator covers at least a portion of the sensor substrate or sensor electrode.

4. The sensor of claim 1, wherein the sensor is implantable within a living animal.

5. The sensor of claim 1, wherein the one or more degradative species probes are co-monomers with the analyte indicator.

6. The sensor of claim 1, wherein the one or more degradative species probes are co-monomers with the analyte indicator in a hydrogel.

7. The sensor of claim 2, wherein the one or more degradative species probes are entrapped in a hydrogel covering at least a portion of the sensor housing.

8. The sensor of claim 1, wherein the one or more degradative species probes bind to the degradative species.

9. The sensor of claim 1, wherein the one or more degradative species probes reduce chemical degradation and/or oxidation of the analyte indicator.

10. The sensor of claim 1, wherein the one or more degradative species probes sequester the degradative species so as to reduce, and/or prevent degradation of the analyte indicator by the degradative species.

11. The sensor of claim 1, wherein the analyte indicator comprises a polymer comprising co-monomers of four monomers according to Formula IX: A_B_C_D [Formula IX],
wherein A is an analyte indicator monomer, B is a methacrylate monomer, C is a polyethylene glycol monomer, and D is the one or more degradative species probes, wherein A is 0.01 to 10% by weight, B is 1 to 99% by weight, C is 1 to 99% by weight, and D is 0.01 to 99% by weight of the total polymer.

12. The sensor of claim 1, wherein the one or more degradative species probes are provided at a molar ratio of 0.1 to 100 to analyte indicator monomer.

13. The sensor of claim 1, wherein the sensor comprises a mixture of two or more of the degradative species probes.

14. A method of fabricating a sensor for measurement of an analyte in a medium within a living animal, the method comprising:
applying an analyte indicator to a sensor such that the applied analyte indicator covers at least a portion of the sensor, wherein the analyte indicator comprises one or more degradative species probes, wherein the degradative species probes have absorption and/or emission profiles that are selective for a specific degradative species, wherein the one or more degradative species probes comprise:
(a) a degradative species probe of Formula I:

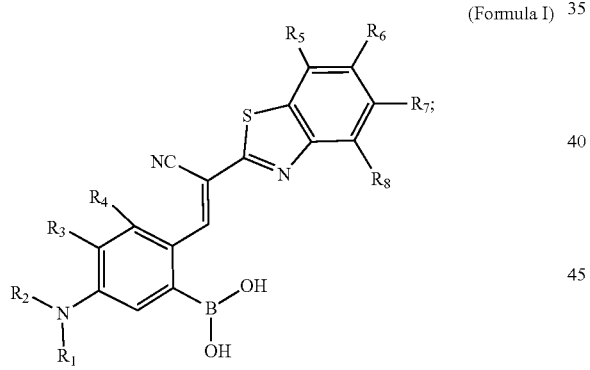

(Formula I)

(b) a degradative species probe of Formula II:

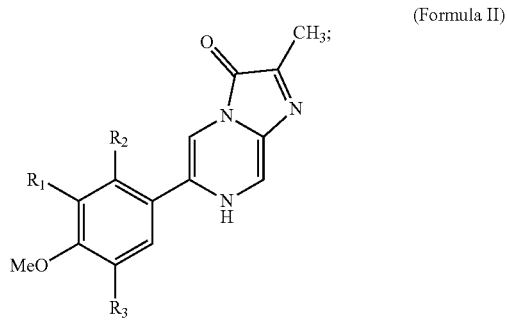

(Formula II)

(c) a degradative species probe of Formula IV:

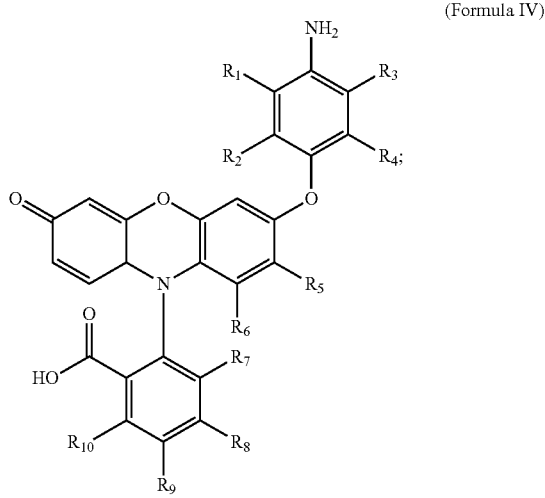

(Formula IV)

(d) the degradative species probe of the Formula I and the degradative species probe of the Formula II;
(e) the degradative species probe of the Formula II and the degradative species probe of the Formula IV;
(f) the degradative species probe of the Formula I and the degradative species probe of the Formula IV; or
(g) the degradative species probe of the Formula I, the degradative species probe of the Formula II, and the degradative species probe of the Formula IV,
wherein each R1, R2, R3, R4, R5, R6, R7, R8, R9, and R10 is independently selected from the group consisting of H, C1-C20 alkyl, C1-C20 alkoxy, carboxy, aryl, heteroaryl, polycyclic, alkoxy, halide, SH, aryloxy, alkylthio, amino, substituted amino, alkoxycarbonyl, alkanoylamido, aroylamido, heterocyclocarbonylamido, heteroaroylamido, alkanoyl(alkylsubstituted) amido, aroyl(alkylsubstituted)amido, heteroaroyl(alkylsubstituted)amido, and heterocyclocarbonyl(alkyl substituted)amido.

15. The method of claim 14, wherein the one or more degradative species probes are co-monomers with the analyte indicator.

16. The method of claim 14, wherein the one or more degradative species probes are co-monomers with the analyte indicator in a hydrogel.

17. The method of claim 14, further comprising a sensor housing, wherein the one or more degradative species probes are entrapped in a hydrogel covering at least a portion of the sensor housing.

18. The method of claim 14, wherein the one or more degradative species probes reduce chemical degradation and/or oxidation of the analyte indicator.

19. The method of claim 14, wherein the one or more degradative species probes interact or react with a degradative species, wherein the degradative species is hydrogen peroxide, a reactive oxygen species, a reactive nitrogen species, an enzyme, a free radical or a metal ion.

20. The method of claim 14, wherein the one or more degradative species probes bind to the degradative species.

21. The method of claim 14, wherein the one or more degradative species probes sequester the degradative species so as to reduce, and/or prevent degradation of the analyte indicator by the degradative species.

22. The method of claim 14, wherein the analyte indicator comprises a polymer comprising co-monomers of four monomers according to Formula IX: A-B-C-D [Formula IX], wherein A is an analyte indicator monomer, B is a methacrylate monomer, C is a polyethylene glycol monomer, and D is the one or more degradative species probes, wherein A is 0.01 to 10% by weight, B is 1 to 99% by weight, C is 1 to 99% by weight, and D is 0.01 to 99% by weight of the total polymer.

23. The method of claim 14, wherein the one or more degradative species probes are provided at a molar ratio of 0.1 to 100 to analyte indicator monomer.

24. The method of claim 14, wherein the sensor comprises a mixture of two or more of the degradative species probes.

25. The sensor of claim 1, wherein the one or more degradative species probes further comprise:

(i) a degradative species probe of Formula V:

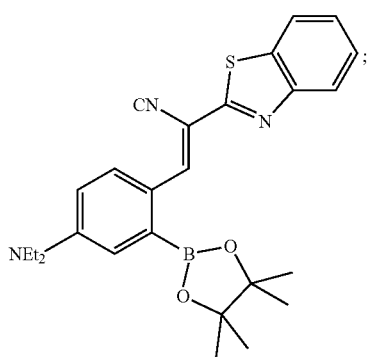

(Formula V)

(ii) a degradative species probe of Formula VI:

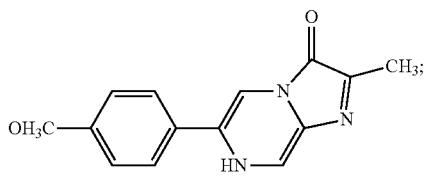

(Formula VI)

(iii) a degradative species probe of Formula VIII:

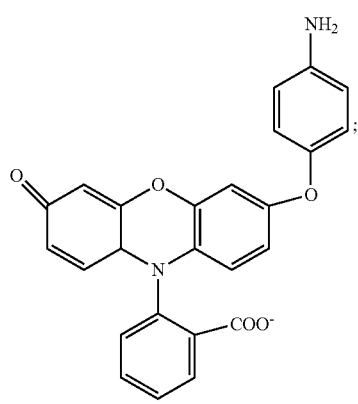

(Formula VIII)

(iv) the degradative species probe of the Formula V and the degradative species probe of the Formula VI;

(v) the degradative species probe of the Formula V and the degradative species probe of the Formula VIII;

(vi) the degradative species probe of the Formula VI and the degradative species probe of the Formula VIII; or (vii) the degradative species probe of the Formula V, the degradative species probe of the Formula VI, and the degradative species probe of the Formula VIII.

26. The sensor of claim 1, wherein the one or more degradative species probes further comprise a degradative species probe of Formula V:

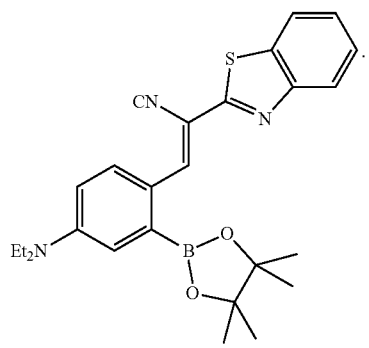

(Formula V)

27. The sensor of claim 1, wherein the one or more degradative species probes further comprise a degradative species probe of Formula VI:

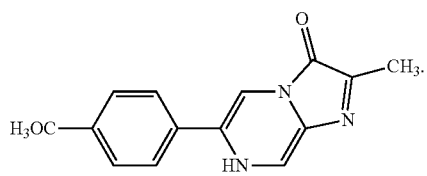

(Formula VI)

28. The sensor of claim 1, wherein the one or more degradative species probes further comprise a degradative species probe of Formula VIII:

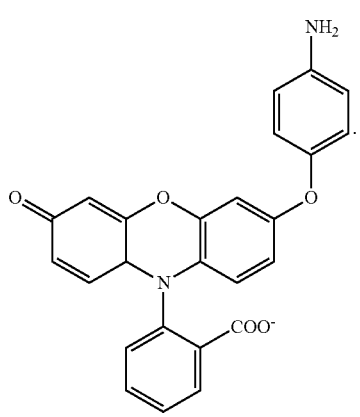

(Formula VIII)

29. The sensor of claim 1, wherein the one or more degradative species probes comprise the degradative species probe of the Formula I.

30. The sensor of claim 1, wherein the one or more degradative species probes comprise the degradative species probe of the Formula II.

31. The sensor of claim 1, wherein the one or more degradative species probes comprise the degradative species probe of the Formula IV.

32. The method of claim 14, wherein the one or more degradative species probes comprise the degradative species probe of the Formula I.

33. The method of claim 14, wherein the one or more degradative species probes comprise the degradative species probe of the Formula II.

34. The method of claim 14, wherein the one or more degradative species probes comprise the degradative species probe of the Formula IV.

\* \* \* \* \*